United States Patent
Giri et al.

(10) Patent No.: US 11,969,355 B2
(45) Date of Patent: Apr. 30, 2024

(54) SPINAL CAGE WITH MODULAR ANCHORING ELEMENTS

(71) Applicant: CTL Medical Corporation, Addison, TX (US)

(72) Inventors: Bala K Giri, Dallas, TX (US); Jon Suh, Ambler, PA (US); Sean Suh, Milltown, NJ (US)

(73) Assignee: CTL Medical Corporation, Addison, TX (US)

( * ) Notice: Subject to any disclaimer, the term of this patent is extended or adjusted under 35 U.S.C. 154(b) by 225 days.

(21) Appl. No.: 17/334,555

(22) Filed: May 28, 2021

(65) Prior Publication Data

US 2022/0241088 A1 Aug. 4, 2022

Related U.S. Application Data

(60) Provisional application No. 63/143,767, filed on Jan. 29, 2021.

(51) Int. Cl.
*A61F 2/44* (2006.01)
*A61F 2/30* (2006.01)

(52) U.S. Cl.
CPC .......... *A61F 2/4455* (2013.01); *A61F 2/447* (2013.01); *A61F 2002/30433* (2013.01); *A61F 2002/30482* (2013.01); *A61F 2002/30604* (2013.01)

(58) Field of Classification Search
CPC .......... A61F 2/44; A61F 2/4455; A61F 2/446; A61F 2/4465; A61F 2/447; A61F 2002/30433; A61F 2002/30482; A61F 2002/30604
See application file for complete search history.

(56) References Cited

U.S. PATENT DOCUMENTS

| | | | | |
|---|---|---|---|---|
| 7,850,731 B2* | 12/2010 | Brittan | .................. | A61F 2/4611 623/17.11 |
| 8,641,766 B2* | 2/2014 | Donner | .................. | A61B 17/92 606/279 |
| 9,968,461 B2* | 5/2018 | Zappacosta | ............ | A61F 2/4455 |
| 10,052,212 B2* | 8/2018 | Fiechter | ............... | A61F 2/4465 |
| 10,179,053 B2* | 1/2019 | Zappacosta | ............. | A61F 2/447 |
| 10,925,750 B2* | 2/2021 | Zappacosta | ............. | A61F 2/447 |
| 11,638,650 B2* | 5/2023 | Valkoun | .................. | A61F 2/447 623/17.16 |
| 2006/0085071 A1* | 4/2006 | Lechmann | ............ | A61F 2/4465 623/17.11 |
| 2014/0012380 A1* | 1/2014 | Laurence | ............... | A61F 2/4465 623/17.16 |
| 2014/0039623 A1* | 2/2014 | Iott | ..................... | A61F 2/30744 623/17.16 |
| 2022/0241088 A1* | 8/2022 | Giri | ..................... | A61F 2/30749 |

* cited by examiner

*Primary Examiner* — Eric S Gibson
(74) *Attorney, Agent, or Firm* — BRAINSPARK ASSOCIATES, LLC

(57) ABSTRACT

The invention relates to a modular anchoring adaptor that engages with existing features of commercially available ALIF cages to help eliminate migration and/or anterior expulsion cause by the instability of the spine, such as lordosis. Such modular adaptor will mate or engage with existing features to enhance anchoring within the vertebral disc space, which space is limited and a low-profile should be maintained.

20 Claims, 9 Drawing Sheets

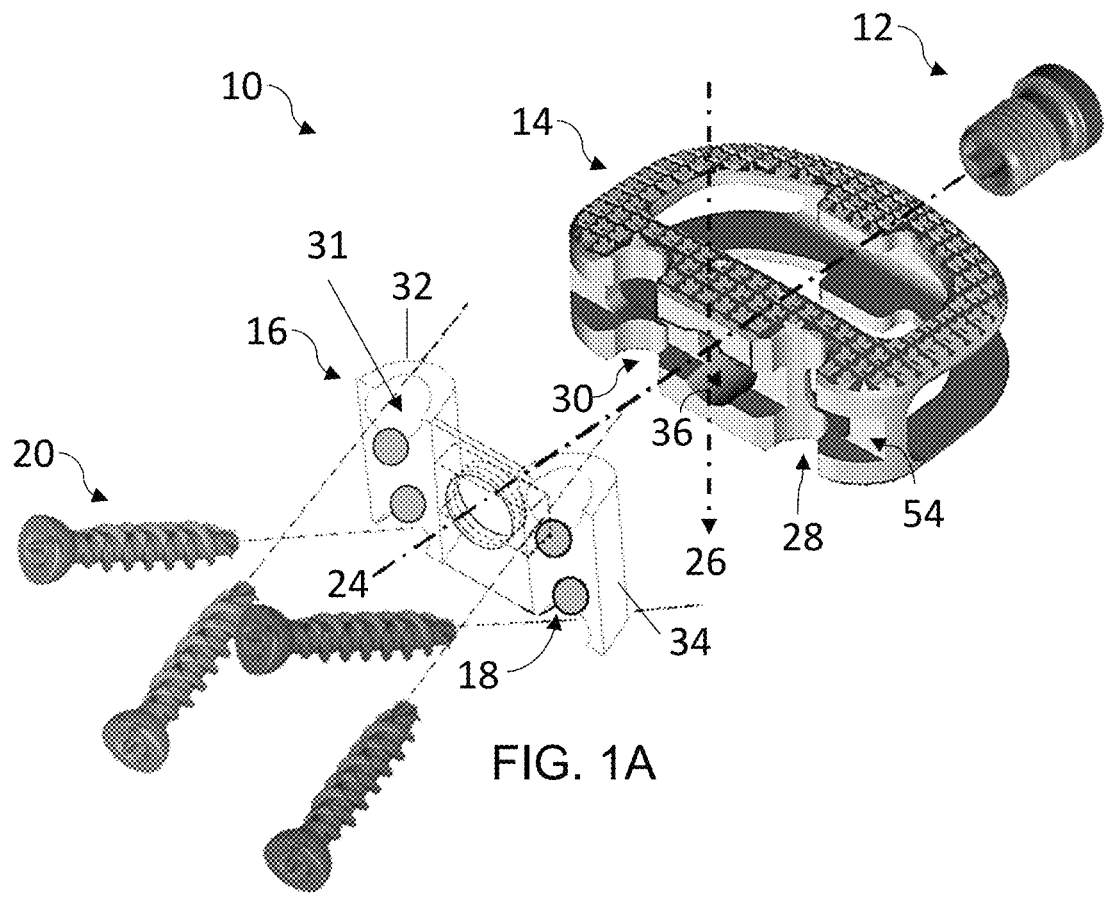
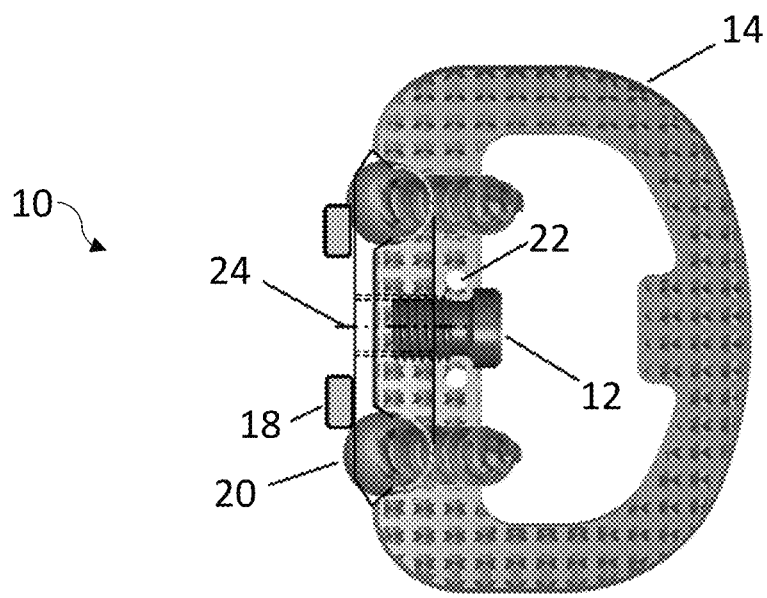

SPINAL CAGE WITH MODULAR ANCHORING ELEMENTS

CROSS-REFERENCE TO RELATED APPLICATIONS

This application claims the benefit of U.S. Provisional Application No. 63/143,767 entitled "Spinal Cage with Modular Anchoring Elements" filed Jan. 29, 2021, the disclosure of which is incorporated by reference herein in its entirety.

TECHNICAL FIELD

The invention relates to methods, devices, and systems for an improved spinal cage with modular anchoring elements to help eliminate migration and/or anterior expulsion caused by scoliosis, kyphosis, lordosis, spinal stenosis, etc. More specifically, the invention relates to a modular anchoring adaptor that engages with existing features of commercially available ALIF cages to help eliminate migration and/or anterior expulsion where space may be limited.

BACKGROUND OF THE INVENTION

The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition, congenital or acquired deformities can cause abnormal angulation or slippage of the spine. Anterior slippage (spondylolisthesis) of one vertebral body on another can cause compression of the spinal cord or nerves. Patients who suffer from one of more of these conditions often experience extreme and debilitating pain and can sustain permanent neurological damage if the conditions are not treated appropriately.

Alternatively, or in addition, there are several types of spinal curvature disorders. Examples of such spinal curvature disorders include, but need not be limited to, lordosis, kyphosis and scoliosis.

One technique of treating spinal disorders, in particular the degenerative, traumatic and/or congenital issues, is via surgical arthrodesis of the spine. This can be accomplished by removing the intervertebral disk and replacing it with implant(s) and/or bone and immobilizing the spine to allow the eventual fusion or growth of the bone across the disk space to connect the adjoining vertebral bodies together. The stabilization of the vertebra to allow fusion is often assisted by the surgically implanted device(s) to hold the vertebral bodies in proper alignment and allow the bone to heal, much like placing a cast on a fractured bone. Such techniques have been effectively used to treat the above-described conditions and in most cases are effective at reducing the patient's pain and preventing neurological loss of function.

The spinal curvature disorders and/or contour issues present on the surfaces of the vertebrae may present additional challenges. As such, there is need for further improvement, and the present subject matter is such improvement. Currently, traditional ALIF cages contain ineffective designs to help reduce or eliminate migration and/or anterior expulsion. Typically, surgeons insert a screw on the anterior face of the vertebrae directed diagonally to allow the screw head to partially occlude the anterior face of the ALIF cage. Alternatively, there are other ALIF designs that require a full plate that is coupled to the anterior face of the upper and lower vertebrate with additional insertion tools and fixation screws, which the plate does not engage with the implanted ALIF design. These traditional designs are less cost effective and may not be useful when there is only a limited amount of space available.

BRIEF SUMMARY OF THE INVENTION

The following presents a simplified summary of the subject matter in order to provide a basic understanding of some aspects of the subject matter. This summary is not an extensive overview of the subject matter. It is intended to neither identify key or critical elements of the subject matter nor delineate the scope of the subject matter. Its sole purpose is to present some concepts of the subject matter in a simplified form as a prelude to the more detailed description that is presented later.

Disclosed is an implant device for the spine, the implant device being desirably sized and configured for location between two adjacent vertebrae. Various features of the present invention include the realization of a need for a variety of anchoring systems and/or components that can be modularly connected to an interbody spinal cage or other implant to desirably reduce and/or minimize movement of the cage or other implant relative to the adjacent anatomical surfaces. In many embodiments, the modular anchoring component can incorporate a various of designs and/or configurations that can accommodate various anatomical constraints and/or conditions, including unique anatomical conditions that may facilitate and/or constrain one or more attachment modalities and/or portions thereof. In some embodiments, a surgical kit containing a plurality of modular anchoring components that can each be attached to an interbody spinal cage or other implant (with a plurality of such interbody spinal cages or other implants optionally included in the kit) can greatly reduce the number and/or extent of kit components necessary for a given surgery, with commensurate reductions in the cost and/or complexity of the implant kit.

In one exemplary embodiment, a modular adapter ALIF cage system can comprise: an ALIF cage assembly, the ALIF cage assembly comprising a cage, the cage including a longitudinal axis, a superior surface, an inferior surface, an anterior surface and a posterior surface, the anterior surface comprising a cage opening, a first groove and a second groove, the first groove and second groove are spaced apart and are parallel to the longitudinal axis, the cage opening positioned between the first groove and second groove; and a modular adapter, the modular adapter comprising a first post, the first post comprising a first end and a second end, the first post sized and configured to engage with the first or second groove of the cage. The modular adapter further comprises a second post, the second post comprising a first end and a second end, the second post sized and configured to engage with the first or second groove of the cage. The modular adapter further comprises a plate, the plate extends between the first post and the second post, the plate comprising a plate opening, the plate opening is concentric with the cage opening. The first end or the second end of the first post comprises a keel, the keel extends away in the posterior direction. The first end or the second end of the second post comprises a keel, the keel extends away in the posterior direction. The at least one of the first end or the second end of the first post and second post comprises a keel, each of the keels extends away in the posterior direction. The first end or a second of the first post including a scallop, the scallop oriented obliquely, the scallop sized and configured to receive a portion of at least one fixation screw. Alternatively, the first end or the second of the second post including a scallop, the scallop oriented obliquely, the scallop sized and configured to receive a portion of at least one fixation screw. The first end or the second end of the first post and the second post comprising a scallop, each of the scallops oriented obliquely, each of the scallops sized and configured to receive a portion of at least one fixation screw. An anterior facing surface of the modular adapter is colinear with an anterior facing surface of adjacent vertebral bodies. Alternatively, an anterior facing surface of the modular adapter is offset behind an anterior face surface of adjacent vertebral bodies (offset in a posterior direction). Furthermore, the ALIF cage system is sized and configured to fit between the adjacent vertebral bodies.

In another exemplary embodiment, the modular adapter ALIF cage system can comprise: an ALIF cage assembly, the ALIF cage assembly comprising a cage and a set screw, the cage including a superior surface, an inferior surface, an anterior surface and a posterior surface, the anterior surface comprising an cage opening, a first groove and a second groove, the first groove and second groove are spaced apart and are parallel to the longitudinal axis, the opening positioned between the first groove and second groove; and a modular adapter, the modular adapter comprising a first post, a second post, and a plate, the plate extends between the first post and second post, the first and second post are spaced apart and align with the first groove and second groove of the body, the plate including an plate opening, the plate opening being concentric with the cage opening, the first post engages with the first groove of the anterior surface of the cage, the second post engages with the second groove of the anterior surface of the cage, the set screw inserted through the cage opening and the plate opening to secure the modular adapter to the cage. The at least one of the first post and second post comprises a first end, a second end, and a keel, the keel is disposed onto a first end, extending away from the first end towards a posterior direction. Alternatively, each of the first post and second post comprises a first end, a second end, and a first keel and a second keel, the first and second keels are disposed onto a first end of the first post and second post, extending away from the first end towards a posterior direction. Furthermore, the at least one of the first post or second post comprises a first end and a second end, the first end or the second end including a scallop, the scallop oriented obliquely, the scallop sized and configured to receive a portion of at least one fixation screw. The at least one of the first post or the second post comprises a first end and a second end, each of the first end and the second end including a scallop, the scallops oriented obliquely, the scallops sized and configured to receive a portion of at least one fixation screw. The at least one of the first post or the second post comprises first end and a second end, the first end or second end further including a cam lock, the cam lock movable from a first position to a second position, the first position being an open position allowing a portion of a fixation screw to disposed onto the scallop, and the second position being a closed position allowing the cam lock to cover a portion of the fixation screw to prevent migration. The anterior surface of the cage further comprises a third groove, the third groove is positioned perpendicular to the first or second groove and between the superior and inferior surface of the cage. The plate further comprises an extension member, the extension member sized and configured to engage with the third groove. An anterior surface of the modular adapter is colinear with an anterior surface of adjacent vertebral bodies. Alternatively, an anterior facing surface of the modular adapter is offset behind an anterior face surface of adjacent vertebral bodies (offset in a posterior direction). Furthermore, the ALIF cage system is sized and configured to fit between the adjacent vertebral bodies.

BRIEF DESCRIPTION OF THE SEVERAL VIEWS OF THE DRAWINGS

The foregoing and other features and advantages of the present subject matter will become apparent to those skilled in the art to which the present subject matter relates upon reading the following description with reference to the accompanying drawings.

FIG. 1A-1B depicts an isometric and top view of one embodiment of a modular adapter ALIF cage system;

FIGS. 4A-4F depicts multiple views of one embodiment of an ALIF cage;

DETAILED DESCRIPTION OF THE INVENTION

Figure 2A:
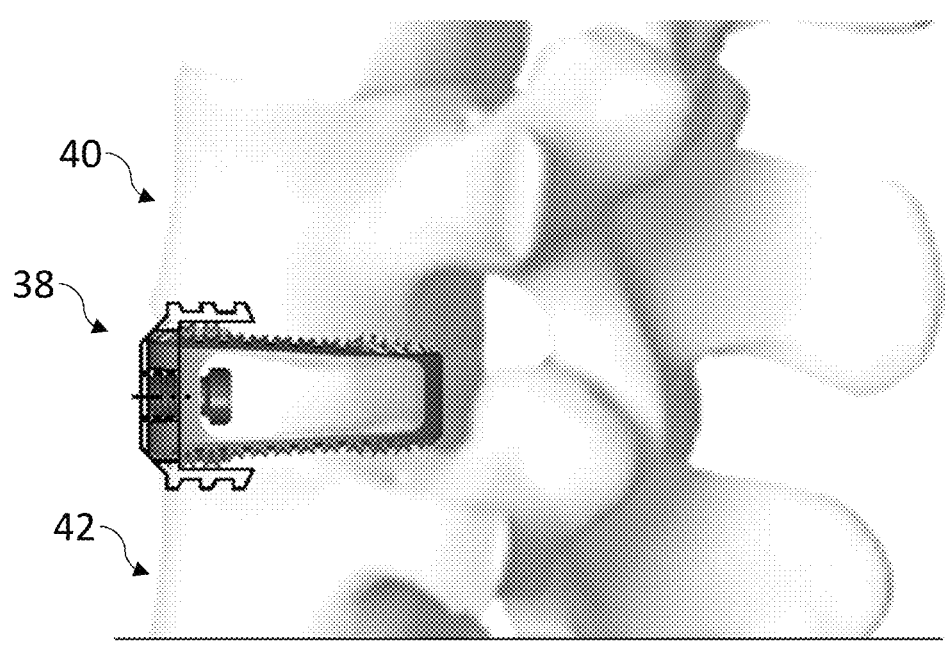
FIGS. 2A-2C depicts a side and top view of an alternate embodiment of a modular adapter ALIF cage.
Figure 2B:
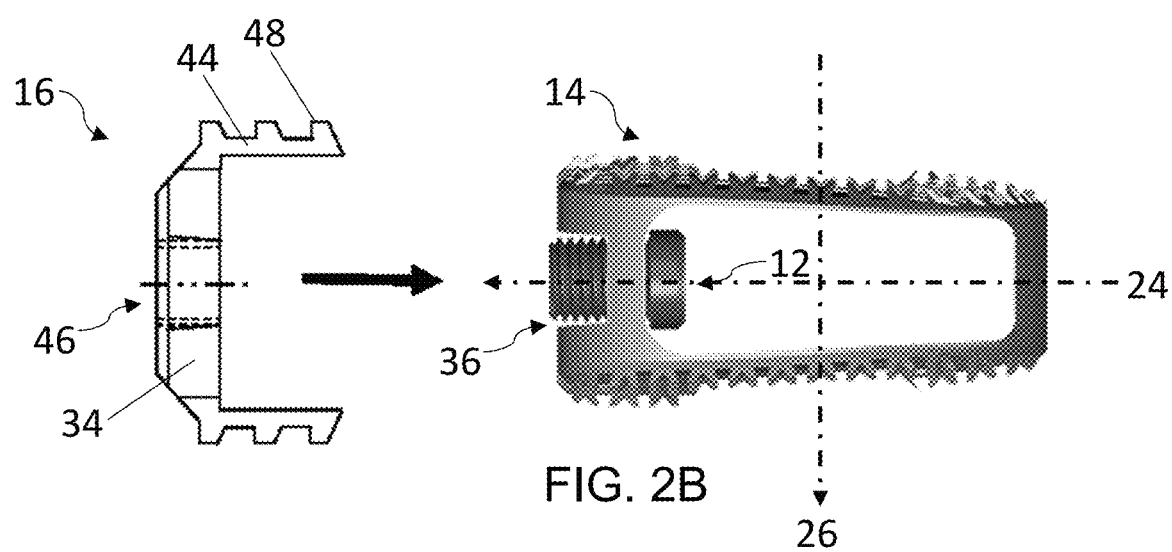
Figure 2C:
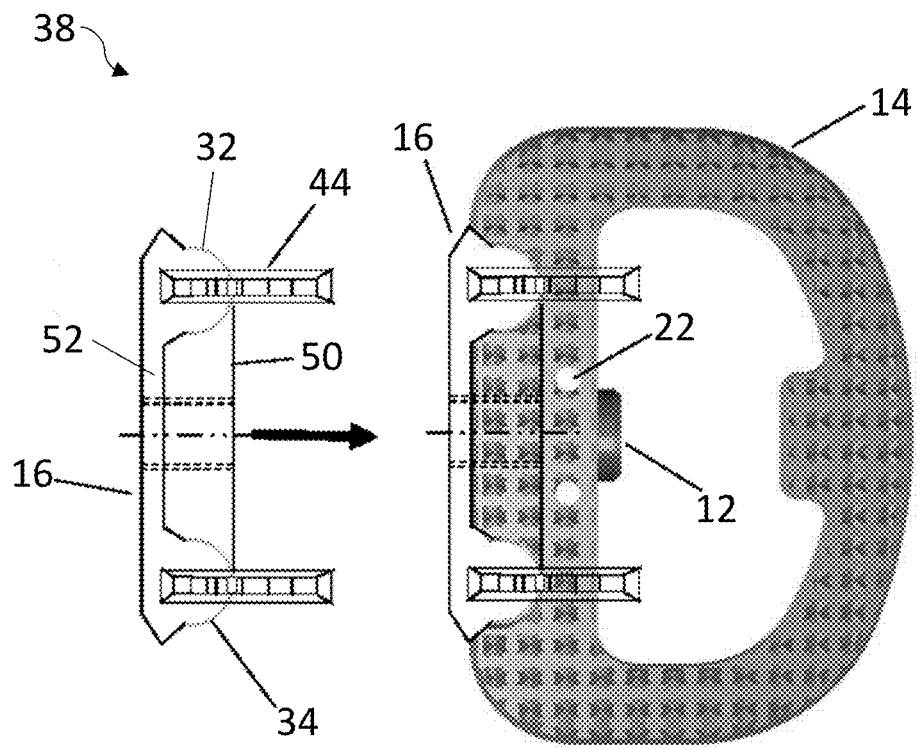
Figure 3:
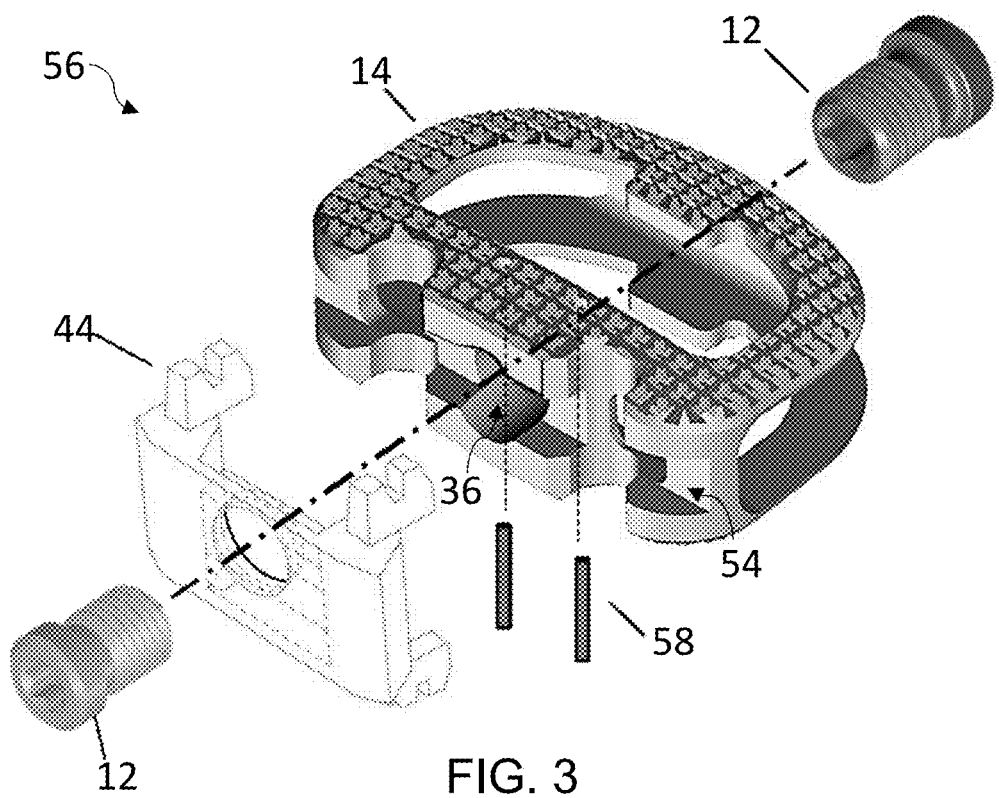
FIG. 3 depicts a side and top view of an alternate embodiment of a modular adapter ALIF cage.

The present subject matter relates generally to devices for the fixation and support of vertebrae. In particular, the present subject matter relates to implant devices that can incorporate a variety of modular anchoring components. In various embodiments, the anchoring components are modularly connected to an interbody spinal cage or other implant to desirably reduce and/or minimize movement of the cage or other implant relative to the adjacent anatomical surfaces. In many embodiments, the modular anchoring component can incorporate a various of designs and/or configurations that can accommodate various anatomical constraints and/or conditions, including unique anatomical conditions that may facilitate and/or constrain one or more attachment modalities and/or portions thereof. In some embodiments, a surgical kit containing a plurality of modular anchoring components that can each be attached to an interbody spinal cage or other implant (with a plurality of such interbody spinal cages or other implants optionally included in the kit) can greatly reduce the number and/or extent of kit components necessary for a given surgery, with commensurate reductions in the cost and/or complexity of the implant kit.

As is known in the art, a spinal column desirably provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition, congenital or acquired deformities can cause abnormal angulation or slippage of the spine. Anterior slippage (spondylolisthesis) of one vertebral body on another can cause compression of the spinal cord or nerves. Patients who suffer from one of more of these conditions often experience extreme and debilitating pain, and can sustain permanent neurological damage if the conditions are not treated appropriately.

Alternatively or in addition, there are several types of spinal curvature disorders. Examples of such spinal curvature disorders include, but need not be limited to, lordosis, kyphosis and scoliosis.

Aside from the challenges presented by the limited access, size and angulation of various surgical approaches to the spinal anatomy, spinal curvature disorders and/or contour issues can often present on the surfaces of the vertebrae, which may present additional challenges.

The present subject matter will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present subject matter. It may be evident, however, that the present subject matter can be practiced without these specific details. Additionally, other embodiments of the subject matter are possible and the subject matter is capable of being practiced and carried out in ways other than as described. The terminology and phraseology used in describing the subject matter is employed for the purpose of promoting an understanding of the subject matter and should not be taken as limiting.

Figure 4A:
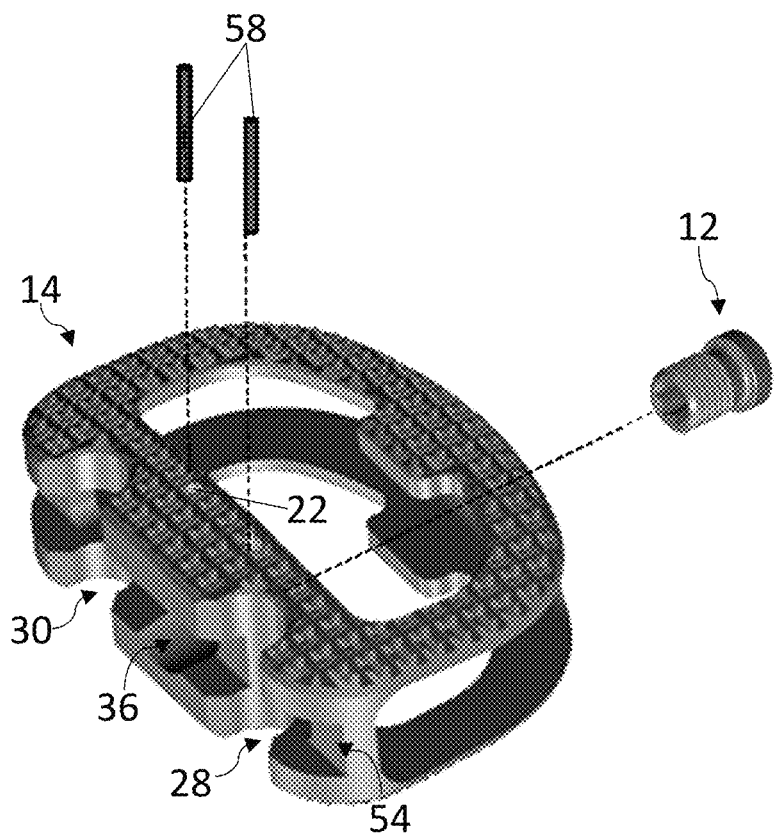
FIGS. 4A-4B depicts a side and top view of an alternate embodiment of a modular adapter ALIF cage.
Figure 4B:
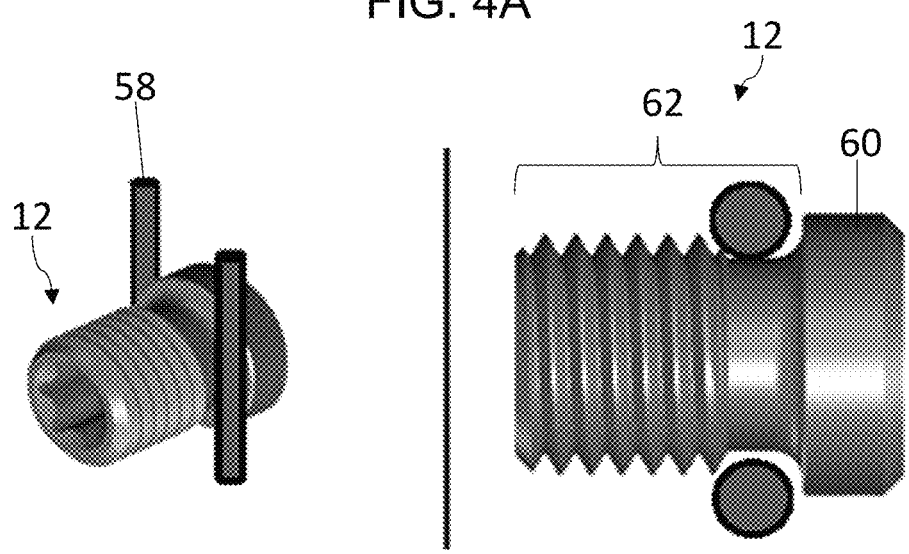
Figure 4C:
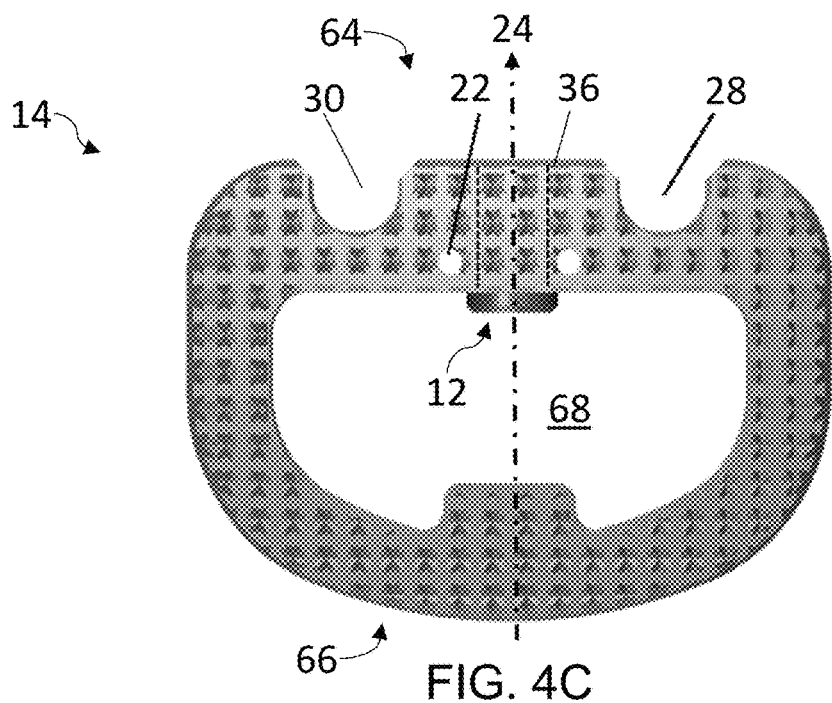
Figures 4D, 4E:
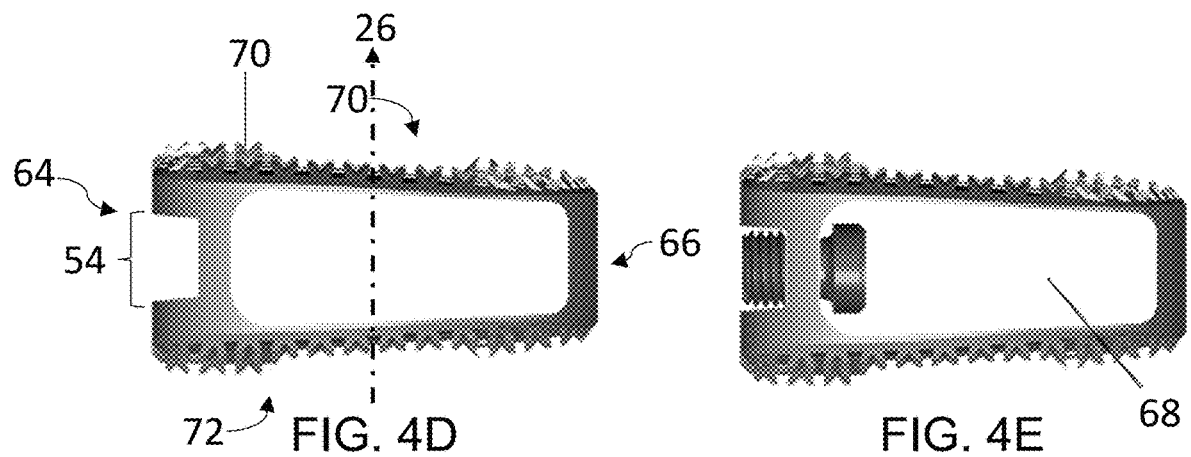
Figure 4F:
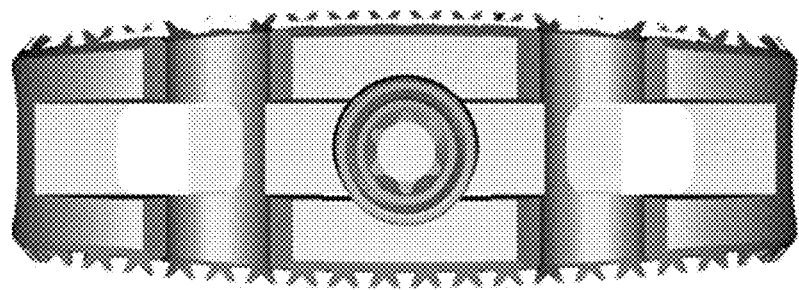

FIGS. 1A-1B depict one embodiment of a modular adapter ALIF cage system 10. The modular adapter ALIF cage system 10 comprises an interbody implant or cage 14, a set screw 12, and a modular adapter 16. The modular adapter ALIF cage system 10 further comprises one or more fixation screws 20. The cage 14 includes a longitudinal axis 26, a superior surface 70, an inferior surface 72, an anterior surface 64 and a posterior surface 66, the anterior surface 64 comprising a cage opening 36 and a plurality of grooves 28,30 (refer to FIGS. 4C-4E). The plurality of grooves 28,30 are spaced apart and parallel to the longitudinal axis 26. The plurality of grooves 28,30 are sized and configured to receive a portion of a plurality of posts 32,34 of the modular adapter 16. The cage opening 36 positioned between the plurality of groves 28,30, the cage opening 36 may be concentric or parallel to an axial axis 24 of the cage 14. The cage 14 further comprises one or more plurality pin openings 22, the one or more pin openings 22 disposed onto the superior surface of the cage 14. The cage 14 further comprises a plurality dowel pins 58 that are sized and configured to be disposed into the plurality of pin openings 22. The plurality of dowel pins 58 contact or engage with a portion of the bottom surface of the set screw head 60 and/or a portion of the thread body 62 to prevent migration as shown in FIGS. 4A-4B.

The cage 14 may further comprise a textured surface 70. The textured surface may be disposed onto the anterior surface 64, the posterior surface 72, the superior surface 70, the inferior surface 72, and/or any combinations thereof.

The modular adapter 16 comprises a plurality of posts 32,34 that are sized and configured to engage with each of the plurality of grooves 28,30. The plurality of posts 32,34 comprises a first end and a second end. The modular adapter 16 further comprises a plate opening that is concentric with the cage opening 36. The plurality of posts 32,34 of the modular adapter 16 may further comprise one or more scallops 31. The one or more scallops 31 may be oriented obliquely, and are desirably sized and/or configured to accommodate and/or capture more than 180 degrees of the circumference of the head of a fixation screw 20 or other securement device. The one or more scallops may be disposed onto the first end or the second end of the plurality of posts 32,34, or the one or more scallops may be disposed onto the first end and the second end of plurality of posts 32,34. Alternatively, the one or more scallops may be disposed onto the first end or the second end of each of the plurality of posts 32,34, or the one or more scallops may be disposed onto the first end and the second end of each of the plurality of posts 32,34. In various embodiments, such as depicted in FIG. 1A, at least a portion of a head of one or more fixation screws 20 can extend outward of an exterior surface of the modular adapter 16 while being adequately retained by the scallop 31.

The modular adapter 16 further comprises a cam lock 18, the cam lock 18 positioned or disposed onto a first end or a second end of the plurality of posts 32,34, or the cam lock 18 positioned or disposed onto a first end and the second end of the plurality of posts 32,34. Alternatively, the cam lock 18 positioned or disposed onto a first end or a second end of each of the plurality of posts 32,34, or the cam lock 18 positioned or disposed on a first end and a second end of each of the plurality of posts 32,34. The cam lock 18 can be movable from a first position to a second position, the first position being an open position allowing a portion of a fixation screw 20 to be disposed onto and/or into the one or more scallops, and the second position being a closed position allowing the cam lock 18 to cover and/or block a portion of the fixation screw 20 to prevent migration. In various embodiments, the cam lock 18 may simply inhibit counterrotation or loosening of the screw from the bone, while in other embodiments the cam lock 18 may compress and secure the screw to the modular adapter 16 in an immovable fashion.

FIGS. 2A-2C and 3 depicts a side view and a top view of an alternate embodiment of a modular adapter ALIF cage system 38,56. The modular adapter ALIF cage system 38,56 comprises an anterior facing surface that is colinear with the adjacent vertebral bodies 40,42. Alternatively, the modular adapter ALIF cage system 38,56 may comprise an anterior facing surface that is positioned posterior to the anterior facing surface of the adjacent vertebral bodies 40,42. In another embodiment, the modular adapter ALIF cage system 38 comprises an anterior facing surface that extends or slightly extends beyond the anterior facing surface of the adjacent vertebral bodies 40,42. Accordingly, the modular adapter ALIF cage system 38 may be sized and configured to fit between the adjacent vertebral bodies 40,42.

The modular adapter ALIF cage system 38,56 comprises a cage 14, a set screw 12, and a modular adapter 16. The cage 14 including a longitudinal axis 26, a superior surface, an inferior surface, an anterior surface and a posterior surface, the anterior surface comprising a cage opening 36 and a plurality of grooves 28,30. The plurality of grooves 28,30 are spaced apart and parallel to the longitudinal axis 26. The plurality of grooves 28,30 are sized and configured to receive a portion of a plurality of posts 32,34 of the modular adapter 16. The cage opening 36 positioned between the plurality of groves 28,30, the cage opening 36 may be concentric or parallel to an axial axis 24 of the cage 14. The cage 14 further comprises one or more plurality pin openings 22, the one or more pin openings 22 disposed onto the superior surface of the cage 14. The cage 14 further comprises a plurality dowel pins 58 that are sized and configured to be disposed into the plurality of pin openings 22. The plurality of dowel pins 58 contact or engage with a portion of the bottom surface of the set screw head 60 and/or a portion of the thread body 62 to prevent migration as shown in FIGS. 4A-4B.

The modular adapter 16 comprises a plurality of posts 32,34 that are sized and configured to engage with the plurality of grooves 28,30 and/or each of the plurality of grooves 28,30. The plurality of posts 32,34 comprises a first end and a second end. The modular adapter 16 further comprises a plate opening 46 that is concentric with the cage opening 36. The modular adapter 16 may further comprise a rib 50, the rib 50 may be positioned between the plurality of posts 32,34. The rib 50 may extend between the plurality of posts 32,34. Alternatively, the rib 50 may be disposed on a plate 52, the plate 52 extends between the plurality of posts 32,34. The rib 50 may extend posteriorly, the rib 50 may be sized and configured to be disposed into a third groove 54 on the cage 14, and/or the rib 50 may be sized and configured to engage with the third groove 54 on the cage 14.

The plurality of posts 32,34 of the modular adapter 16 may further comprise a keel 44, and/or each of the plurality of posts 32,34 comprises a keel 44. The keel 44 may be disposed onto a first end or second end of the plurality of posts 32,34, and/or the keel 44 may be disposed onto a first end and a second end of the plurality of posts 32,34. Alternatively, the keel 44 may be disposed onto a first end or second end of each of the plurality of posts 32,34, and/or the keel 44 may be disposed onto a first end and a second end of each of the plurality of posts 32,34. The keel 44 extends toward a posterior direction, the keel 44 comprising one or more teeth that extend upwardly to contact or engage with the adjacent vertebral bodies 40,42.

Figure 5A:
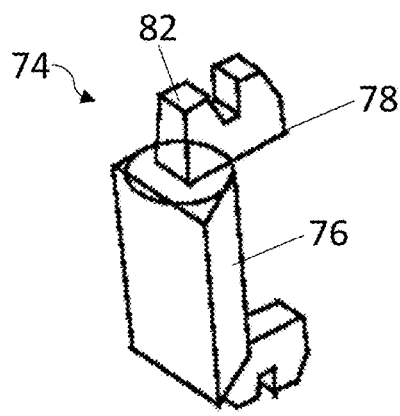
FIGS. 5A-5B depicts an isometric view of one embodiment of a modular adapter.
Figure 5B:
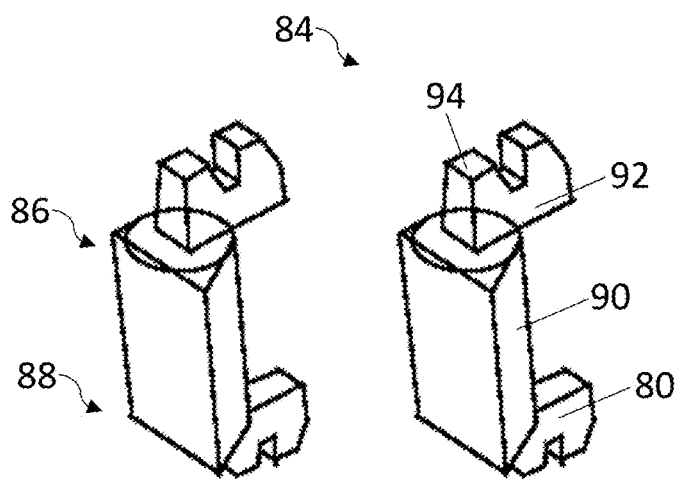

FIGS. 5A-5B depicts an isometric view of one embodiment of a modular adapter 74,84. The modular adapter 74,84 comprises at least one post 76 and at least one keel 78,80. The at least one post 76 comprises a first end 86 and a second end 86. The at least one post 76 comprises a size and configuration to mate and/or engage with the plurality of grooves and/or the first or second groove of the cage. Alternatively, the at least one post 76 comprises at least one surface that mates and/or engages with the plurality of grooves and/or the first and/or second groove of the cage. The first end 86 and/or the second end 86 of the at least one post 76 comprises a keel 78. The keel 78 may be positioned perpendicular or substantially perpendicular to the first end 86 and/or the second end 88. The keel 78 extends away in a posterior direction, the keel 78 includes one or more teeth 82 that extend upwardly to contact or engage with the adjacent vertebral bodies 40,42.

In another embodiment, the modular adapter 74,84 comprising a first post 76 a second post 90, the first post 76 and the second post 90 are spaced apart and align with the first groove and second groove of the cage. The first post 76 and second post 90 comprises a first end 86 and a second end 88. The first 86 or second end 88 of the first post comprises a keel 78. Accordingly, the first 86 and the second end 88 of the first post 76 comprises a keel 78. The second post 90 comprises a first end and a second end. The first or second end of the second post 90 comprising a keel 92. The first end and second end of the second post 90 comprising a keel 92. The keel 78,92 is disposed onto a first end of the first post 76 or second post 90 extending away towards a posterior direction. Alternatively, the keel 78,92 is disposed onto a second end of the first post 76 or second post 90 extending away towards a posterior direction. The keel 78,92 may be positioned perpendicular or substantially perpendicular to the first end 86 and/or the second end 88. The keel 78,92 extends away in a posterior direction, the keel 78,92 includes one or more teeth 82,94 that extend upwardly to contact or engage with the adjacent vertebral bodies 40,42.

Figure 6A:
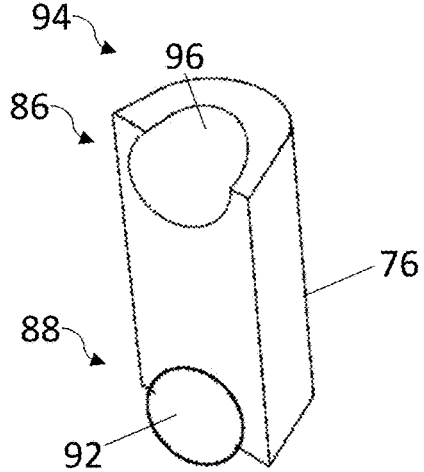
FIGS. 6A-6B depicts an isometric view of an alternate embodiment of a modular adapter.
Figure 6B:
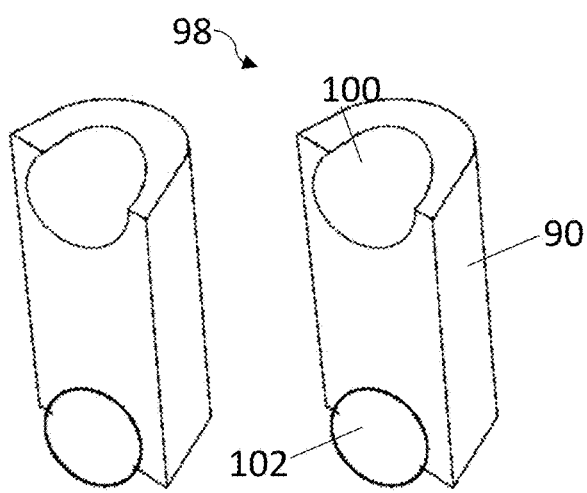

FIGS. 6A-6B depicts an isometric view of an alternative embodiment of a modular adapter 94,98. The modular adapter 94,98 comprises at least one post 76,102. The at least one post 76,90 comprises a first end 86 and a second end 88. The at least one post 76,90 further comprises at least one scallop 96,100. The at least one scallop 96,100 may be disposed on a first end 86 or a second end 88, and/or on a first end 86 and a second end 88. The at least one scallop 96,100 may be oriented obliquely. The at least one scallop 96,100 may comprise a plurality of scallops 96,100. The plurality of scallops 96,100 and/or each of the plurality of scallops 96,100 include the same oblique orientation or different oblique orientation. The at least one scallop 96,100 sized and configured to receive a portion of at least one fixation screw (not shown). Accordingly, the at least one scallop 96,100 sized and configured to receive a portion of a head of at least one fixation screw (not shown). The at least one post 76,90 may further comprise a cam lock 92,102. The cam lock 92,102 may be disposed on first end 86 or a second end 88, and/or a first end 86 and a second 88. The cam lock 92,102 movable from a first position to a second position, the first position being an open position allowing a portion of a fixation screw to disposed onto the at least one scallop 96,100, and the second position being a closed position allowing the cam lock 92,102 to cover a portion of the fixation screw and/or the fixation screw head to prevent migration.

Figure 7:
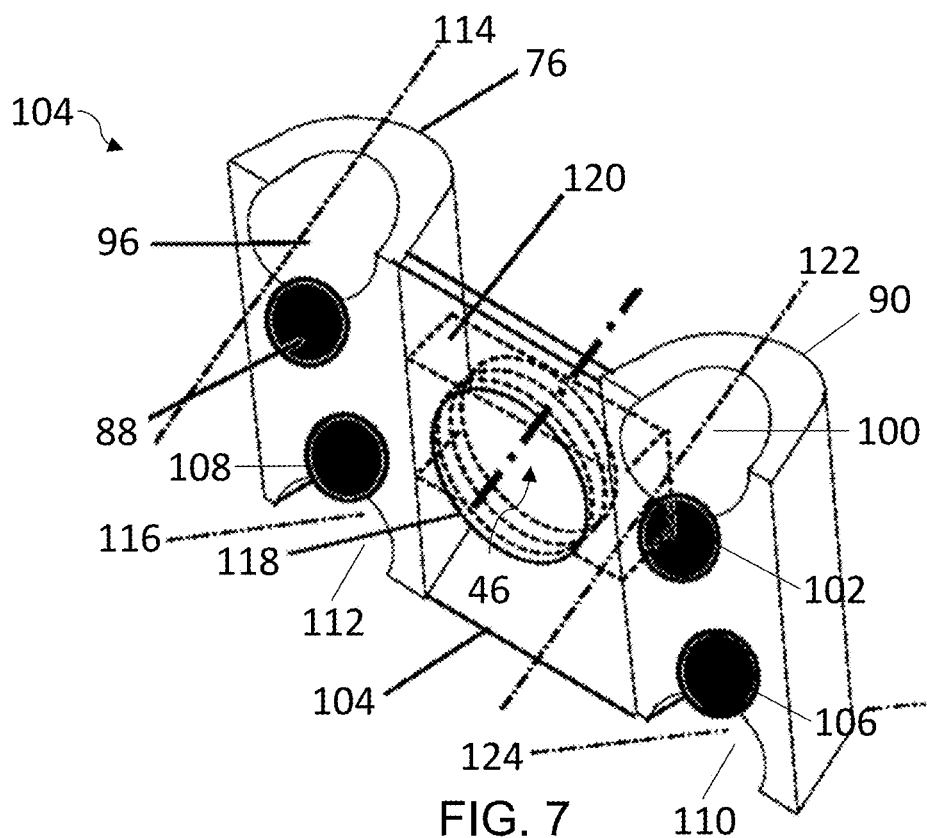
FIG. 7 depicts an isometric view of an alternate embodiment of a modular adapter.

FIG. 7 depicts an isometric view of another alternative embodiment of a modular adapter 104. The modular adapter 104 comprises a plate 104, a first post 76 and a second post 90. The plate 104 extends between the first post 76 and the second post 90. The plate 104 includes a plate opening 46, the plate opening 46 may further comprise threads 118. The plate opening 46 aligns with the cage opening and/or it is concentric with the cage opening. The plate opening 46 is sized and configured to receive a portion of a set screw. The plate 104 may further comprise a rib 120. The rib 120 extends between the first post 76 and the second post 90. The rib 120 extends outwardly in the posterior direction, the rib 120 is sized and configured to be disposed within the third groove of the cage. The rib 120 aligns with or is colinear with the third groove of the cage and/or it will mate and/or engage within the third groove of the cage.

The first post 76 comprises a first end and a second end, the second post 90 comprises a first end or a second end. The first end and a second end of the first post 76 comprises a first scallop 96 and a second scallop 112. The first scallop 96 includes a first orientation 114 and the second scallop 112 includes a second orientation 116. The first orientation 114 and/or the second orientation 116 may include a same oblique angle or a different oblique angle. The first orientation 114 and/or the second orientation 116 may include a same perpendicular angle or a different perpendicular angle. The first end and a second end of the second post 90 comprises a third scallop 100 and a fourth scallop 110. The first end comprises a third scallop 100 and the second end comprises a fourth scallop 110. The third scallop includes a third orientation 122 and the fourth scallop 110 includes a fourth orientation 124. The third orientation 122 and the fourth orientation 124 may include the same angle or a different angle. The angle may include an oblique angle or a perpendicular angle. Accordingly, the first orientation 114, the second orientation 116, the third orientation 122 and/or the fourth orientation 124 may include the same angle or a different angle. The angle includes an oblique angle and/or a perpendicular angle.

Figure 8:
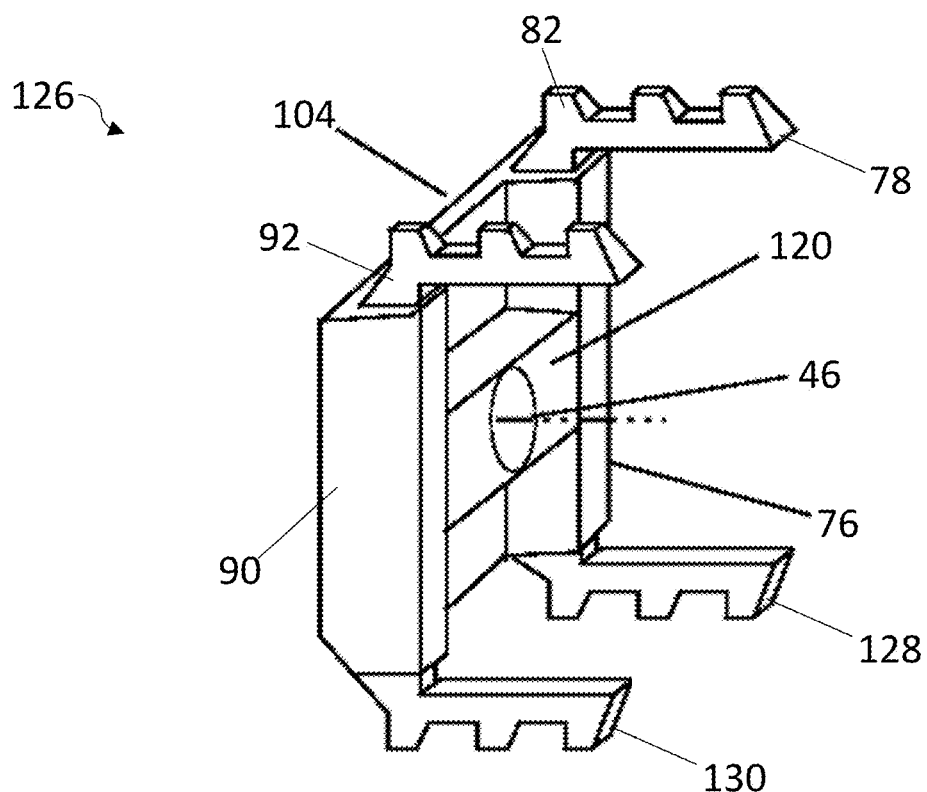
FIG. 8 depicts an isometric view of an alternate embodiment of a modular adapter.
Figure 9A:
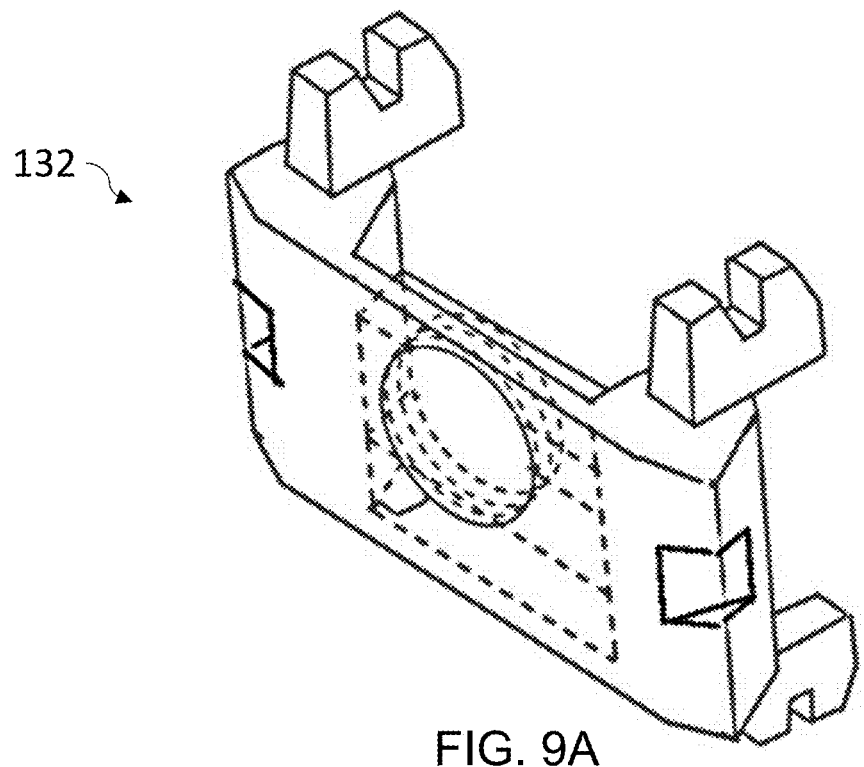
FIGS. 9A-9B depicts an isometric view of an alternate embodiment of a modular adapter.
Figure 9B:
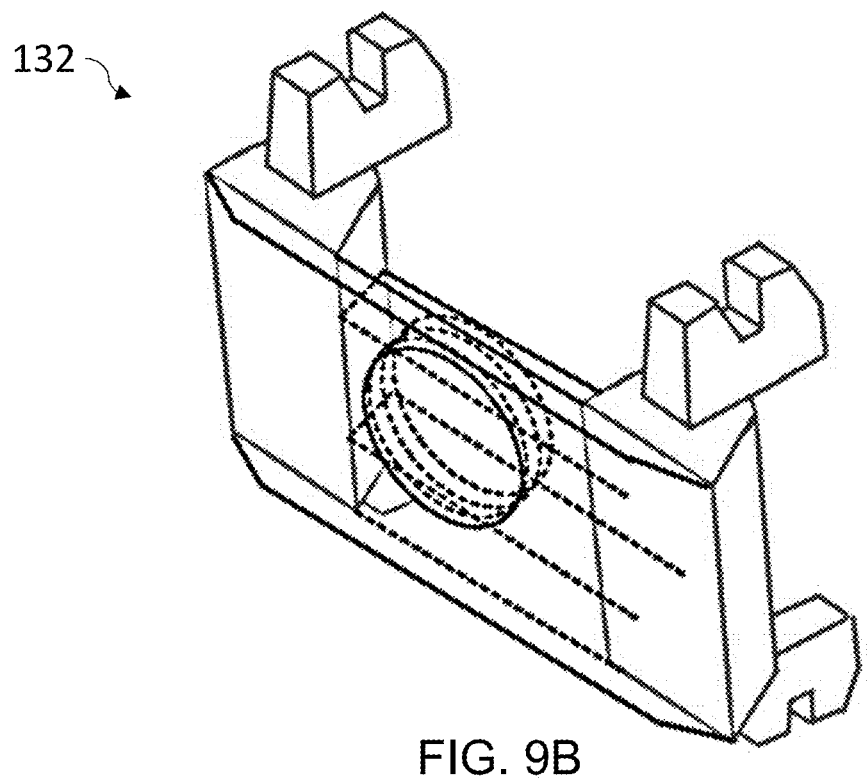

FIGS. 8 and 9A-9B depicts isometric views of additional alternative embodiments of a modular adapter 126 and 132. The modular adapter 104 comprises a plate 104, a first post 76 and a second post 90. The plate 104 extends between the first post 76 and the second post 90. The plate 104 includes a plate opening 46, the plate opening 46 may further comprise threads 118. The plate opening 46 aligns with the cage opening and/or it is concentric with the cage opening. The plate opening 46 is sized and configured to receive a portion of a set screw. The plate 104 may further comprise a rib 120. The rib 120 extends between the first post 76 and the second post 90. The rib 120 extends outwardly in the posterior direction, the rib 120 is sized and configured to be disposed within the third groove of the cage. The rib 120 aligns with or is colinear with the third groove of the cage and/or it will mate and/or engage within the third groove of the cage.

The first post 76 comprises a first end and a second end, the second post 90 comprises a first end or a second end. The first end and a second end of the first post 76 comprises a first keel 78 and a second keel 128. The first keel 78 and a second keel 128 extending away towards a posterior direction. The first keel 78 and/or the second keel 128 may be positioned perpendicular or substantially perpendicular to the first end and/or the second end. The first keel 78 and/or the second keel 128 includes one or more teeth 82 that extend upwardly to contact or engage with the adjacent vertebral bodies 40,42. The second post 90 comprises a first end and a second end. The first end and a second end of the second post 90 comprises a third keel 92 and a fourth keel 130. The third keel 92 and a fourth keel 130 extending away towards a posterior direction. The first keel 78 and/or the fourth keel 130 may be positioned perpendicular or substantially perpendicular to the first end and/or the second end. The third keel 92 and/or the fourth keel 130 includes one or more teeth 82 that extend upwardly to contact or engage with the adjacent vertebral bodies 40,42.

Figure 10A:
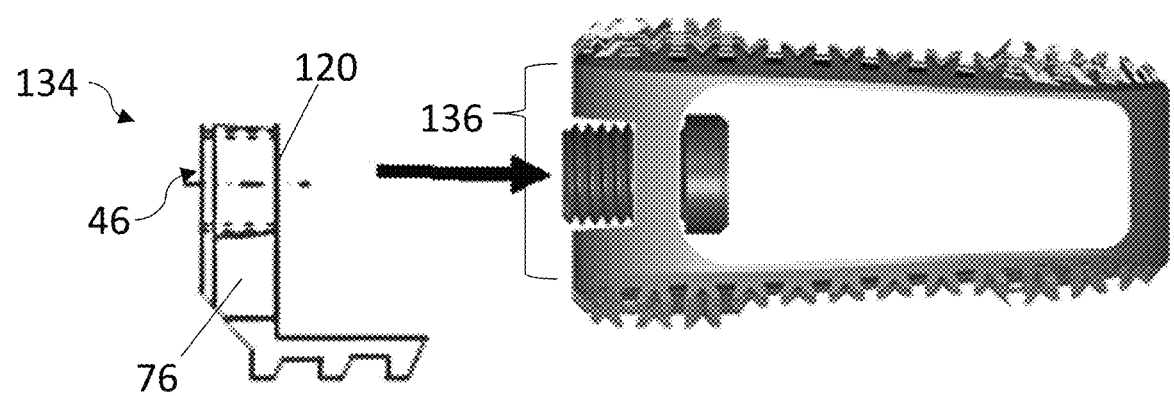
FIGS. 10A-10B depicts an isometric view of an alternate embodiment of a modular adapter.
Figure 10B:
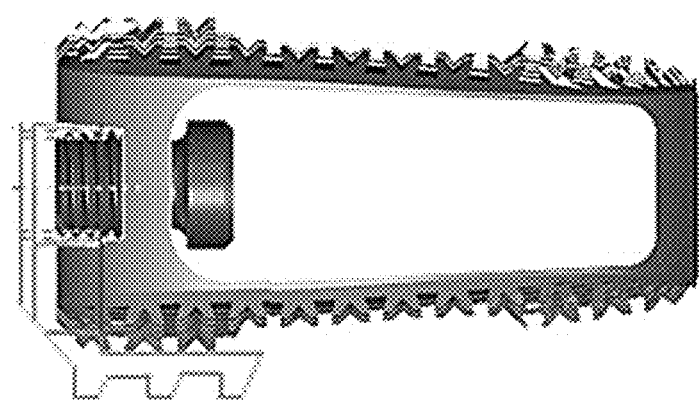

FIGS. 10A-10B depicts an additional alternative embodiment of a modular adapter 134. The modular adapter 134 comprises a plate 120, a first post 76 and a second post 90 (not shown). The first post 76 including a first length and the second post 90 including a second length. The first length and/or the second length extending along a portion of the anterior surface length 136. A plate 120 extending between the first post 76 and the second post 90. The plate 120 comprising a plate opening 46, the plate opening 46 concentric with the cage opening. The plate 120 further comprises a rib 120, the rib 120 extends between the first post 76 and the second post. The rib 120 mates or engages with a third groove of the cage. The rib 76 is disposed adjacent to the first end of the first ends of the first post 76 and the second post 90. A first keel is disposed onto a second end of a first post 76, and a second keel is disposed onto a second post 90. The keels extend toward a posterior direction, the keels comprise on or more teeth that extend upwardly to contact the adjacent vertebral bodies.

In the disclosed embodiments, various locking/securing mechanisms/means, if desired, are contemplated to help retain the device and/or components thereof in a specific adjustment (e.g., at least some distance of the respective engagement areas are adjusted). If desired, the implant device may have more or fewer components, and/or the number and distribution of links or other connecting features such as pins may vary accordingly. The devices may include exterior ridges, grooves, teeth, surface roughening, porous coatings or other treatments which enhance fixation to bone and/or bone ingrowth or on growth. The disclosed devices may further include one or more clamps, clips, clasps, braces, snapping mechanisms or other locking devices to hold the device in the compact configuration or in the expanded configuration. Such locking devices may be integral to the interbody device or may be entities separate from the interbody device. The various devices described herein may further include one or more biasing elements to bias the device toward the compact configuration or toward the expanded configuration.

In various embodiment, method(s) for manufacturing the disclosed devices and/or implanting the device into a spine are contemplated and are part of the scope of the present application.

Devices and/or components thereof that are in communication with each other need not be in continuous communication with each other, unless expressly specified otherwise. In addition, devices that are in communication with each other may communicate directly or indirectly through one or more intermediaries.

Although process steps, method steps, or the like, may be described in a sequential order, such processes and methods may be configured to work in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure. While embodiments and applications of the present subject matter have been shown and described, it should be apparent to those skilled in the art that many more modifications are possible without departing from the inventive concepts herein. The subject matter, therefore, is not to be restricted except in the spirit of the appended claims. Thus, while embodiments and applications of the present subject matter have been shown and described, it should be apparent that other embodiments, applications and aspects are possible and are thus contemplated and are within the scope of this application.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A modular adapter ALIF cage system comprising:
an ALIF cage assembly, the ALIF cage assembly comprising a cage and a set screw, the cage including a superior surface, an inferior surface, an anterior surface and a posterior surface, the anterior surface comprising a cage opening, a first groove and a second groove, the first groove and the second groove are spaced apart and are parallel to a longitudinal axis of the cage extending through the superior surface and the inferior surface, the opening positioned between the first groove and the second groove; and
a modular adapter, the modular adapter comprising a first post, a second post, and a plate, the plate extends between the first post and second post, the first and second posts are spaced apart and align with the first groove and second groove, the plate including a plate opening, the plate opening being concentric with the cage opening, the first post engages with the first groove of the anterior surface of the cage, the second post engages with the second groove of the anterior surface of the cage,
the set screw inserted through the cage opening and the plate opening to secure the modular adapter to the cage, wherein at least one of the first post and the second post comprises a first end, a second end, and a keel disposed onto the first end, the keel extending away from the first end to overlie at least a portion of the cage.

2. The modular adapter ALIF cage system of claim 1, wherein each of the first post and the second post include a keel which overlies at least a portion of the cage.

3. The modular adapter ALIF cage system of claim 1, wherein at least one of the first post or the second post comprises a first scallop, the first scallop oriented obliquely relative to an axial axis of the cage, the first scallop sized and configured to receive a portion of at least one fixation screw.

4. The modular adapter ALIF cage system of claim 3, wherein the at least one of the first post or the second post comprises a second scallop spaced apart from the first scallop, the second scallop sized and configured to receive a portion of a second fixation screw.

5. The modular adapter ALIF cage system of claim 3, wherein at least one of the first post or the second post comprises a cam lock movable from a first position to a second position, the first position being an open position allowing a portion of a fixation screw to be disposed onto the first scallop, and the second position being a closed position allowing the cam lock to cover a portion of the fixation screw to prevent migration.

6. The modular adapter of ALIF cage system of claim 1, wherein the anterior surface of the cage further comprises a third groove, the third groove is positioned perpendicular to the first or second groove and between the superior and inferior surface of the cage.

7. The modular adapter of ALIF cage system of claim 6, wherein the plate further comprises an extension member, the extension member sized and configured to engage with the third groove.

8. The modular adapter ALIF cage system of claim 1, wherein an anterior surface of the modular adapter is configured to be colinear with an anterior surface of at least one adjacent vertebral body.

9. A modular adapter ALIF cage system comprising:
an ALIF cage assembly, the ALIF cage assembly comprising a cage and a set screw, the cage including a longitudinal axis, a superior surface, an inferior surface, an anterior surface and a posterior surface, the anterior surface comprising a cage opening, a first groove and a second groove, the first groove and the second groove are spaced apart and are parallel to the longitudinal axis, the cage opening positioned between the first groove and the second groove; and
a modular adapter, the modular adapter comprising a first post, the first post comprising a first end and a second end, the first post sized and configured to engage with the first groove or the second groove wherein the first end or the second end of the first post comprises a first keel which overlaps at least a first portion of the cage.

10. The modular adapter ALIF cage system of claim 9, wherein the modular adapter further comprises a second post, the second post configured to engage with the first or second groove of the cage.

11. The modular adapter ALIF cage system of claim 10, wherein the modular adapter further comprises a plate, the plate extends between the first post and the second post, the plate comprising a plate opening, the plate opening is concentric with the cage opening.

12. The modular adapter ALIF cage system of claim 11, wherein the set screw is inserted through the plate opening and the cage opening to secure the modular adapter to the cage.

13. The modular adapter ALIF cage system of claim 10, wherein the second post comprises a second keel, the second keel overlapping at least a second portion of the cage.

14. The modular adapter ALIF cage system of claim 13, wherein at least a portion of the cage is positioned between the first and second keels.

15. The modular adapter ALIF cage system of claim 10, wherein the the second post includes a scallop oriented obliquely relative to an axial axis of the cage, the scallop sized and configured to receive a portion of a second fixation screw.

16. The modular adapter ALIF cage system of claim 9, wherein the first end or the second end of the first post includes a first scallop, oriented obliquely relative to an axial axis of the cage, the first scallop sized and configured to receive a portion of a first fixation screw.

17. The modular adapter ALIF cage system of claim 16, wherein the first post includes a second scallop, each of the first and second scallops oriented obliquely relative to an axial axis of the cage, the first scallop being spaced apart from the and second scallop.

18. The modular adapter ALIF cage system of claim 9, wherein an anterior facing surface of the modular adapter is adapted to be colinear with an anterior facing surface of at least one adjacent vertebral body.

19. A modular adapter ALIF cage system comprising:
an ALIF cage assembly, the ALIF cage assembly comprising a cage and a set screw, the cage including a longitudinal axis, a superior surface, an inferior surface, an anterior surface and a posterior surface, the anterior surface comprising a cage opening, a first groove and a second groove, the first groove and the second groove are spaced apart and are parallel to the longitudinal axis, the cage opening positioned between the first groove and the second groove; and
a modular adapter, the modular adapter comprising a first post, the first post comprising a first end and a second end, the first post sized and configured to engage with the first or second groove of the cage,
wherein the first end or the second end of the first post includes a first scallop oriented obliquely relative to an axial axis of the cage, the first scallop sized and configured to receive a portion of at least one fixation screw.

20. The modular adapter ALIF cage system of claim 19, wherein the first post includes a second scallop oriented obliquely relative to the axial axis of the cage, the first scallop being spaced apart from the second scallop.

* * * * *